(12) United States Patent
Thompson et al.

(10) Patent No.: US 7,550,179 B2
(45) Date of Patent: Jun. 23, 2009

(54) METHOD OF COPPER DEPOSITION FROM A SUPERCRITICAL FLUID SOLUTION CONTAINING COPPER (I) COMPLEXES WITH MONOANIONIC BIDENTATE AND NEUTRAL MONODENTATE LIGANDS

(75) Inventors: Jeffrey Scott Thompson, Wilmington, DE (US); Alexander Zak Bradley, Drexel Hill, PA (US); Kyung-Ho Park, Wilmington, DE (US)

(73) Assignee: E.I du Pont de Nemours and Company, Wilmington, DE (US)

( * ) Notice: Subject to any disclaimer, the term of this patent is extended or adjusted under 35 U.S.C. 154(b) by 672 days.

(21) Appl. No.: 11/215,256

(22) Filed: Aug. 30, 2005

(65) Prior Publication Data

US 2006/0099343 A1    May 11, 2006

Related U.S. Application Data

(60) Provisional application No. 60/605,581, filed on Aug. 30, 2004.

(51) Int. Cl.
*C23C 16/00* (2006.01)
(52) U.S. Cl. .................. 427/430.1; 427/250; 427/314
(58) Field of Classification Search .......... 427/430.1
See application file for complete search history.

(56) References Cited

U.S. PATENT DOCUMENTS

| | | | |
|---|---|---|---|
| 4,737,384 A | 4/1988 | Murthy et al. | |
| 4,970,093 A | 11/1990 | Sievers et al. | |
| 5,789,027 A | * 8/1998 | Watkins et al. | 427/250 |
| 6,689,700 B1 | 2/2004 | Watkins et al. | |

FOREIGN PATENT DOCUMENTS

EP    1 024 524 A2    8/2000

OTHER PUBLICATIONS

Lang, H.; Leschke, M.; Melter, M.; Walfort B.; Koehler, K.; Schulz, S.; Gessner, T., Mono- and Bimetallic Copper(I)- and Silver(I)-Phosphane Complexes with β-Diketonate Units, 2003, Wiley-VCH Verlag GmbH & Co. KGaA, Zeitschrift uer Anorganische und Allgemeine Chemie, 629 (12-13), p. 2371-2380.*
X. Ye et. al., Making Nanomaterials in Supercritical Fluids: A Review, J. Chem. Ed., 2003, pp. 198 and 201-203, vol. 80.
Oleg A. Louchev et. al., The Morphological Stability in Supercritical Fluid Chemical Deposition of Films Near the Critical Point, Journal of Crystal Growth, 1995, pp. 276-285, vol. 155.
J.F. Bocquet et. al., The New TIO2 Film Deposition Process in a Supercritical Fluid, Surface and Coatings Technology, 1994, pp. 73-78, vol. 70.
J. Brasseur-Tilmant et. al., Ceramic Membrane Elaboration Using Supercritical Fluid, Materials Research Bulletin, 1999, pp. 2013-2025, vol. 34.

* cited by examiner

*Primary Examiner*—Michael Barr
*Assistant Examiner*—Ryan Schiro
(74) *Attorney, Agent, or Firm*—Gail D. Tanzer

(57) ABSTRACT

Methods of depositing a copper film onto the surface of a substrate from a supercritical solution containing copper-containing precursors having monoanionic bidentate and neutral monodentate ligands, which comprise contacting the substrate with the solution; heating the substrate to a temperature between about 60° C. and less than 150° C.; and forming a copper-containing film on at least a portion of the substrate surface. Also provided are copper-containing precursor compositions used therein.

7 Claims, No Drawings

METHOD OF COPPER DEPOSITION FROM A SUPERCRITICAL FLUID SOLUTION CONTAINING COPPER (I) COMPLEXES WITH MONOANIONIC BIDENTATE AND NEUTRAL MONODENTATE LIGANDS

FIELD OF THE INVENTION

The invention relates to methods of depositing a copper film onto the surface of a substrate from a supercritical solution containing copper-containing precursors, which comprise monoanionic bidentate and neutral monodentate ligands, and to such precursor compositions.

TECHNICAL BACKGROUND

As a technique for the deposition of copper film onto a commercially important substrate, like a silicon wafer, supercritical fluid deposition ["SCFD"], is becoming increasingly important because of its environmental and economic benefits. SCFD is a deposition technique akin to the firmly established technique of chemical vapor deposition ["CVD"]. (See generally, Hitchman et al., eds. (1993) CHEMICAL VAPOR DEPOSITION PRINCIPLES AND APPLICATIONS). SCFD results in copper deposits by heating a solution of an organometallic precursor dissolved in a supercritical fluid.

Supercritical fluid deposition techniques have been reported for about fifteen years. For a synopsis of the history of these techniques, see Ye, X and Wai, C M (2003) Making Nanomaterials in Supercritical Fluids: A Review, *J Chem Ed* 80(2): 198, 201-203. Generally, early supercritical fluid deposition reports demonstrated a variety of chemical deposition mechanisms, such as thermolysis (see Louchev, O A, Popov, V K, Antonov, E and Lemenovski, D A (1995) *Crystal Growth* 155: 276 and Bocquet, J F, Chhor, K and Pommier, C (1994) *Surf and Coat Tech:* 70, 73); or hydrolysis (Brasseur-Tilmant, J, Jestin, P and Pommier, C (1999) *C MaterRes Bull* 34: 2013); or oxidation/nitridation (see EP Patent EP1024524 (2000) to Morita, K, Ohtsuka, T and Ueda, M); or precipitation (see U.S. Pat. No. 4,737,384 (1988) to Murthy et al.) or expansion of a precursor-supercritical solvent solution to fine aerosol which was then injected into a typical CVD reactor (see U.S. Pat. No. 4,970,093 (1990) to Siever et al.)

Recently, Watkins et al. developed a kind of supercritical fluid deposition called chemical fluid deposition ["CFD"], which is a hybrid method that blends the advantages of chemical vapor deposition and electroless plating. See U.S. Pat. No. 6,689,700 (2004) and U.S. Pat. No. 5,789,027 (1998), both of which are hereby incorporated herein by reference. Generally, in CFD the organometallic precursor is dissolved in a supercritical or near-supercritical solution, which is heated to bring about a deposition reaction onto a substrate in contact with the solution. Watkins et al. discusses that metallic precursors may contain variously palladium, platinum, copper, or nickel; that chemical reactions may include reduction, oxidation, or disproportionation; and that substrates may include silicon wafers or a porous solid substrate.

Specifically, deposition of copper via CFD may occur in a two-reaction process in which a seed layer of copper is first deposited onto the substrate and then additional copper is added to the seed layer. The first of the two deposition reactions is typically a disproportionation reaction having the form:

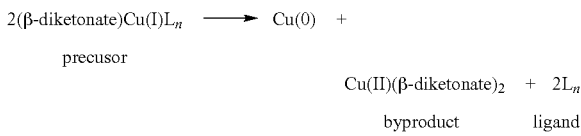

in which L is a neutral ligand and comprises a Lewis base and n may be 1, 2 or a decimal. In this reaction, the copper-containing Cu(I) precursor may be dissolved in a solvent, already at or near a supercritical state. Alternatively, the precursor-solvent may be brought to supercritical conditions after dissolution. In either case, the substrate is heated, which brings about a thermal reduction, i.e., a disproportionation reaction, and results in nonselective deposition of a seed layer of copper onto the substrate surfaces in contact with the solution.

The second reaction is typically a chemical reduction of the disproportionation by-product, Cu(II) (β-diketonate)$_2$ and is brought on by the addition of a reduction reagent, such as H$_2$. In general, the chemical reduction reaction also takes place at the temperature of the disproportionation reaction. The chemical reduction results in selective deposition only onto the copper seed layer surface. This two-step process may also occur simultaneously by adding reducing agent to the supercritical solution before heating.

CFD has great potential in fabricating, especially, copper films or copper wires of widths below 100 nanometers, which serve as interconnects between transistors in integrated circuit boards. Even though olefin and acetylene complexes of β-diketonate copper precursors are generally known, there is still a need to run the deposition reaction at a lower temperature than previously disclosed, for example, lower than disclosed in Watkins et al., supra, for its Cu(hfac) (2-butyne) complexes. This is because the Cu(II) by-products are less likely to decompose at the lower reaction temperature. It is also believed that the Cu(II) by-products are more soluble in scCO$_2$, the preferred supercritical solvent, than their decomposition products. Thus, to maximize utility of CFD for copper deposition, there is a need to use copper-containing precursors, which are not halogenated, and which result in Cu(II) by-products that remain in the supercritical solution.

SUMMARY

Described herein is a method for depositing a copper-containing film onto a surface of a substrate, which comprises dissolving a copper-containing precursor into a solvent such that a supercritical or near-supercritical solution results. The copper-containing precursor has a structural unit represented by the following structure

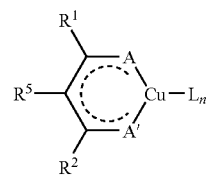

in which L is a neutral ligand selected from a group consisting of alkynes, alkenes, nitrites, diazabutadiene and aromatic nitrogen heterocycles, which are selected from a group consisting of pyridines, pyrazines, triazines, and N-substituted imidazoles, pyrazoles and triazoles. For $L_n$, n is 0.5, 1 or 2. A and A' are O or N-alkyl. When A and A' are both O (oxygen), $R^1$ and $R^2$ are independently selected from a group consisting of methyl, ethyl, propyl, t-butyl, iso-butyl and neopentyl, and $R^5$ is H or C6-C9 alkyl. When A is O (oxygen) and A' is $NR^3$, $R^1$ and $R^2$ are independently selected from a group consisting of methyl, ethyl, propyl, t-butyl, iso-butyl and neopentyl, $R^3$ is selected from a group consisting of methyl, ethyl, and n-propyl, and $R^5$ is H or C6-C9 alkyl. When A is $NR^3$ and A' is $NR^4$, $R^5$ is H, $R^1$ and $R^2$ are independently selected from a group consisting of methyl, ethyl, propyl, t-butyl, iso-butyl and neopentyl, and $R^3$ and $R^4$ are independently selected from a group consisting of methyl, ethyl, and n-propyl. The steps of the method also comprise contacting the substrate with the solution; heating the substrate to a temperature between about 60° C. and less than 150° C., which induces a reaction; and forming a copper-containing film on at least a portion of the substrate surface.

Also described herein are compositions having the following structural unit

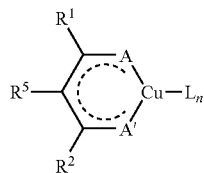

in which L is a neutral ligand selected from a group consisting of alkynes, alkenes, nitrites, diazabutadiene and aromatic nitrogen heterocycles, which are selected from a group consisting of pyridines, pyrazines, triazines, and N-substituted imidazoles, pyrazoles and triazoles. For $L_n$, n is 0.5, 1 or 2. A and A' are O or N-alkyl. When A and A' are both O (oxygen), $R^1$ and $R^2$ are independently selected from a group consisting of methyl, ethyl, propyl, t-butyl, iso-butyl and neopentyl, and $R^5$ is H or C6-C9 alkyl, with the proviso that if $R^1$ and $R^2$ are both t-butyl, then L is a neutral ligand selected from a group consisting of bis(trimethylsilyl)acetylene, 2,2,5,5-tetramethyl-3-hexyne, nitrites, diazabutadiene and aromatic nitrogen heterocycles selected from a group consisting of pyridines, pyrazines, triazines, and N-substituted imidazoles, pyrazoles and triazoles. When A is O (oxygen) and A' is $NR^3$, $R^1$ and $R^2$ are independently selected from a group consisting of methyl, ethyl, propyl, t-butyl, iso-butyl and neopentyl, $R^3$ is selected from a group consisting of methyl, ethyl, and n-propyl, and $R^5$ is H or C6-C9 alkyl. When A is $NR^3$ and A' is $NR^4$, $R^5$ is H, $R^1$ and $R^2$ are independently selected from a group consisting of methyl, ethyl, propyl, t-butyl, iso-butyl and neopentyl, and $R^3$ and $R^4$ are independently selected from a group consisting of methyl, ethyl, and n-propyl, with the proviso that L is not alkene.

DETAILED DESCRIPTION

In this disclosure, a number of terms and abbreviations are used for which the following definitions pertain:

As used herein, "supercritical solvent" refers to a substance heated above its critical temperature and pressurized above its critical pressure to a point at which the substance exists as a gas and liquid in equilibrium. In attaining a density close to or higher than its critical density, a SCF exhibits properties of both a gas and a liquid.

As used herein, "reduction" refers to a reaction in which the oxidation state of an element or compound goes from higher to lower by the gain of one or more electrons and which is accompanied by an oxidation reaction in which the oxidation state of a different element or compound goes from lower to higher by the loss of one or more electrons.

As used herein "disproportionation" refers to the conversion of two like molecules into 2 or more unlike molecules, which is always accomplished by a reduction-oxidation reaction in which some atoms of a single element in a reactant are oxidized and others are reduced. In the disproportionation reactions discussed herein, the Cu ion changes from oxidation state Cu(I) to Cu(II) and Cu(0).

As used herein, "neutral ligand" refers to an unsaturated neutral molecule having alkene or alkyne moiety such as bis(trimethlysilyl)acetylene, or neutral molecule having nitrogen atom such as 1,3,4,5-tetramethylpyrazole.

These terms as well as all other terms may also be clarified by reference to the following dictionaries: the WEBSTER'S THIRD NEW INTERNATIONAL DICTIONARY, UNABRIDGED (1993), Merriam-Webster, Springfield, Mass., and Lewis, R J (2001) HAWLEY'S CONDENSED CHEMICAL DICTIONARY, 14$^{th}$ Ed, John Wiley & Sons, New York, N.Y.

Generally, one method described herein for depositing a copper-containing film onto a surface of a substrate comprises the step of dissolving a copper-containing precursor in a solvent, wherein the dissolving results in a supercritical or near-supercritical solution; wherein the precursor has a structural unit represented by

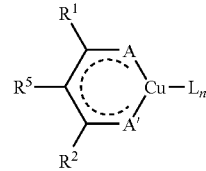

in which L is a neutral ligand selected from a group consisting of alkynes, alkenes, nitriles, diazabutadiene and aromatic nitrogen heterocycles, which are selected from a group consisting of pyridines, pyrazines, triazines, and N-substituted imidazoles, pyrazoles and triazoles. For $L_n$, n is 0.5, 1 or 2. A and A' are O or N-alkyl. When A and A' are both O (oxygen), $R^1$ and $R^2$ are independently selected from a group consisting of methyl, ethyl, propyl, t-butyl, iso-butyl and neopentyl, and $R^5$ is H or C6-C9 alkyl. When A is O (oxygen) and A' is $NR^3$, $R^1$ and $R^2$ are independently selected from a group consisting of methyl, ethyl, propyl, t-butyl, iso-butyl and neopentyl, $R^3$ is selected from a group consisting of methyl, ethyl, and n-propyl, and $R^5$ is H or C6-C9 alkyl. When A is $NR^3$ and A' is $NR^4$, $R^5$ is H, $R^1$ and $R^2$ are independently selected from a group consisting of methyl, ethyl, propyl, t-butyl, iso-butyl and neopentyl, and $R^3$ and $R^4$ are independently selected from a group consisting of methyl, ethyl, and n-propyl. The other steps of the method include contacting the substrate with the solution; heating the substrate to a temperature between about 60° C. and less than 150° C.; and forming a copper-containing film on at least a portion of the substrate surface.

In one method, the substrate may be a porous solid. In an alternative method, the substrate may be copper, silicon or silicon dioxide. In a different method, the substrate comprises a barrier layer. In another method, the solvent comprises carbon dioxide.

In the method described herein, the forming step comprises a disproportionation reaction. This is essentially a reduction-oxidation reaction, in which metallic copper is formed and deposited as a result of a change in the oxidation number of the Cu(I) species of the precursor.

Also described herein are compositions of the copper-containing precursors represented by the general structure

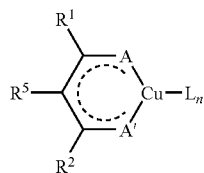

The precursors are Cu(I) compounds, which comprise a bidentate monoanionic ligand. Different compositions herein may use different combinations of nitrogen and oxygen such that A and A' are nitrogen, or both are oxygen, or form a nitrogen-oxygen combination. In all compositions described herein, n is 0.5, 1, or 2, and $R^1$ and $R^2$ are independently selected from a group consisting of t-butyl, iso-butyl and neopentyl. Ligands of this type promote dissolution of the copper complex and the ligand by-products in the solvent.

One composition described herein has a structural unit represented by Structure 2

Structure 2

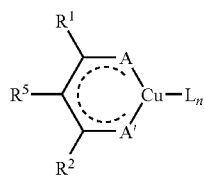

in which L is a neutral ligand selected from a group consisting of alkynes, alkenes, nitriles, diazabutadiene and aromatic nitrogen heterocycles selected from a group consisting of pyridines, pyrazines, triazines, and N-substituted imidazoles, pyrazoles and triazoles. A is O (oxygen). A' is $NR^3$. $R^3$ is selected from a group consisting of methyl, ethyl, and n-propyl. Preferred alkynes include bis(trimethylsilyl)acetylene and 2,2,5,5-tetramethyl-3-hexyne. Preferred alkenes include vinyltrimethylsilane, cyclo-octadiene and norbornene. Preferred nitriles include t-butylnitrile. Preferred aromatic heterocycles include 4-nonylpyridine, 1,3,4,5-tetramethylpyrazole, and 1,2-dimethylimidazole.

Another composition described herein has a structural unit represented by Structure 3

Structure 3

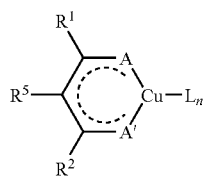

in which L is a neutral ligand selected from a group consisting of bis(trimethylsilyl)acetylene, 2,2,5,5-tetramethyl-3-hex-yne, nitrites, diazabutadiene and aromatic nitrogen heterocycles, which are selected from a group consisting of pyridines, pyrazines, triazines, and N-substituted imidazoles, pyrazoles and triazoles. A and A' are O (oxygen). Preferred nitriles include t-butylnitrile. Preferred aromatic heterocycles include 4-nonylpyridine, 1,3,4,5-tetramethylpyrazole, and 1,2-dimethylimidazole.

A different composition embodiment has a structural unit represented by Structure 4

Structure 4

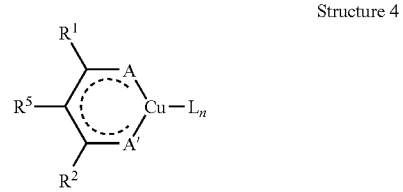

in which L is a neutral ligand selected from a group consisting of alkynes, nitrites, diazabutadiene and aromatic nitrogen heterocycles selected from a group consisting of pyridines, pyrazines, triazines and N-substituted imidazoles, pyrazoles and triazoles. $R^5$ is H, A is $NR^3$ and A' is $NR^4$. $R^3$ and $R^4$ are independently selected from a group consisting of methyl, ethyl, and n-propyl. Preferred alkynes include bis(trimethylsilyl)acetylene and 2,2,5,5-tetramethyl-3-hexyne. Preferred nitrites include t-butylnitrile. Preferred aromatic heterocycles include 4-nonylpyridine, 1,3,4,5-tetramethylpyrazole, and 1,2-dimethylimidazole.

The technical solution of the present invention is the creation of copper-containing precursors designed to achieve maximum solubility in a supercritical solvent, e.g., $scCO_2$. Such solubility is achieved without the usual trifluoromethyl groups but is facilitated by the employment of ligands with branched alkyl groups, $R^1$ and $R^2$, as described above.

The precursors not only possess great solubility in supercritical solvents such as $scCO_2$ but also remain stable at room temperature so that the supercritical solution can be added to the reaction chamber. Their stability means that there is virtually no decomposition in transfer lines, etc. At the same time, the precursors are labile enough to give copper films at relatively low temperatures.

Moreover, the technical solution relates to the fact that the above precursors also provide for soluble and stable by-products. Such by-products do not decompose during the deposition step, unlike the copper-containing precursors in Watkins et al., supra. The technical solution also involves the use of neutral ligands, which are Lewis bases and chosen because, once liberated from the precursor, they also remain soluble in the supercritical solvent at a temperature of between about 60° C. and less than 150° C. In the end, maintaining solubility of the by-products and the neutral ligands minimizes contaminating the copper film with material derived from the ligands and their by-products The ligands are prepared by methodologies similar to those described in the Examples, below. Typically, the β-diketonates are prepared from the corresponding β-diketones, which can, in turn, be prepared by reacting $R^1C(O)OEt$ with a base such as NaH, followed by reaction of the resulting anion with $MeC(O)R^2$ or $R^5CH_2C(O)R^2$. Work-up (e.g., neutralization, filtration, extraction, drying, and distillation) generally gives the β-diketone, $R^1C(O)CH_2C(O)R^2$ or $R^1C(O)CHR^5C(O)R^2$, in relatively pure form, which can be used in the synthesis of the desired copper complex. Generally, the β-diketone is reacted with a base such as NaH in a polar solvent (e.g., an ether). This solution is then added to a mixture of cuprous chloride and an excess of the neutral ligand, L in a polar solvent (e.g., ether). For β-ketoenamines, $R^1C(NR^3)CHR^5C(O)R^2$, or β-diketimines, $R^1C(NR^3)CH_2C(NR^4)R^2$, a base such as n-BuLi or t-BuLi is typically used for deprotonation in ether solvent. McGeachin, S G, (1968) CANADIAN JOURNAL OF CHEMISTRY 46: 1903-1912 describes the synthesis of 1,3-diimines and metal complexes of these ligands, including bis-chelate or homoleptic complexes of the form $ML_2$.

Below is a sampling of common supercritical solvents which may be useful in this invention and their critical points (critical temperature ["$T_c$"] and critical pressure ["$P_c$"]):
ethane ($C_2H_6$): $T_c$=32.3° C., $P_c$=48.2 atm;
trifluoromethane ($CHF_3$): $T_c$=25.6° C., $P_c$=42.9 atm;
hexafluoroethane ($C_2F_6$) $T_c$=19.7° C., $P_c$=30.6 atm; and
carbon dioxide ($CO_2$): $T_c$=31° C., $P_c$=72.8 atm.

$CO_2$ comprises the typical solvent. Hexafluorethane may be used as an alternative. Ethane may also be used, but presents some potential hazards because of its flammability. Dissolution of the precursor in the solvent may occur either before or after the solvent is brought to supercritical conditions.

Solvents used for this process can also comprise co-solvents selected from a group consisting of alcohols and alkanes. Suitable alcohols include methanol and 1-butanol, which are totally miscible with supercritical carbon dioxide at ambient temperatures and high pressure. Compounds showing little or no solubility in hexane or supercritical carbon dioxide can be dissolved with addition of methanol.

Suitable alkanes include C6-C12 alkanes. Between 2 to 5% cosolvent is typically used in order to retain supercritical properties of the solvent at reasonable temperatures and pressures. Higher amounts of co-solvent can be used if the deposition process is run at subcritical conditions. Cross et al. (1996) IND. ENG. CHEM. RES. 35: 1765-1770 describe the use of co-solvents in supercritical carbon dioxide to dissolve metal complexes and is hereby incorporated herein by reference.

Suitable substrates include conducting, semiconducting and insulating substrates, including substrates that are typically used in the electronics industry to manufacture ultra large scale integrated circuits. Suitable substrates typically comprise copper, silicon, silicon dioxide, low k substrates, or low k substrates coated with a barrier layer to prevent the migration of copper. Suitable barrier layers include tantalum, tantalum nitride, titanium, titanium nitride, tantalum silicon nitride, titanium silicon nitride, tantalum carbon nitride, tungsten carbonitride, and niobium nitride. "Low k" substrates have a dielectric constant ("k") less than about 4. Suitable low k substrates include doped oxides (e.g., FSG, HSQ, MSQ, HOSP), organics (e.g., SiLK, BCB, FLARE, PAE), highly fluorinated materials (e.g., parylene-F, a-CF, and PTFE), and porous materials (e.g., aerogel and xerogel). Ultra large integrated circuits typically contain many millions of gates and hundreds of millions of individual transistors.

Temperatures at which the disproportionation reaction, as well as a subsequent or accompanying chemical reduction, occurs in a range between about 60° C. and less than 150° C. The disproportionation reaction occurs when the substrate, especially a silicon wafer, is heated to temperatures between about 60° C. and less than 150° C. Generally only the substrate is heated. However, after sufficient time, the heated substrate, which conducts heat, will warm the solution. The substrate may be heated either before or after it is brought into contact with the supercritical (or near supercritical) solution. Alternatively, the supercritical or subcritical solution can be heated in the presence of the substrate, as illustrated in Example 4 below. The duration of contact can be from less than 0.1 second to more than 1 hour; typically contact times are from 1 second to 10 minutes.

Pressures at which the reactions occur may range from the critical point to about 3000 psi because these pressures facilitate the use of simpler, less expensive equipment. Ultimately there is no upper limit on the pressure range. However, since the precursor compounds of the present invention have great solubility at the critical point, there is typically no need to conduct the reaction at higher pressures. Although higher pressures can generate a denser fluid, which would likely dissolve more material, they do not necessarily provide a benefit.

EXAMPLES

One of skill in the art will appreciate that the selection of temperature, pressure, substrate and specific composition of the precursor will be depend on individual chamber and system design as well as on the desired process rate. The following examples further illustrate, but do not limit, the scope of the invention defined in the claims. All organic reagents and cuprous chloride are available from Sigma-Aldrich Corporation (Milwaukee Wis., USA).

Example 1

Preparation of Bis(trimethylsilyl)acetylene(2,2,7-trimethyloctane-3,5-dionato)copper To a 1 L round bottom flask, to which was fitted a Claisen adapter containing reflux condenser and pressure-equalizing dropping funnel, was added 56 g (60% NaH by weight in mineral oil) of sodium hydride and ethyl trimethylacetate (350 mL). The resultant mixture was stirred with mechanical stirrer under nitrogen, and the flask was fitted with an oil bath. Methyl isobutylketone (88 mL) was added to the dropping funnel. Stirring was begun, and heat was applied until the ester came to a low reflux. The ketone was added at a rate such that the entire volume was added over 4-5 hrs. Heating was continued for an additional hour, after which time the green-yellow mixture was cooled to room temperature and stirred overnight.

Dry toluene (about 300 mL) was added to the mixture, and the mixture was stirred for one hour. The reaction flask was packed in an ice bath, and 120 mL of absolute ethanol was added via a dropping funnel (caution: hydrogen is evolved and foaming occurs). Following the ethanol, 300 mL of 18% (6 M) HCl was slowly added. When the neutralization was completed, the mixture was filtered through a coarse-pore sintered glass funnel. The organic layer was isolated, and dried over anhydrous sodium sulfate. The bulk of the ester and alcohol was removed by rotary evaporation. The residue was then vacuum distilled (distilled temperature; 44° C., vacuum pump pressure; 210 mtorr,) to afford 1,3-diketone (55 g, 42% yield).

Cuprous chloride (1.5 g) was mixed with bistrimethylsilylacetylene (2.582 g) in ether (30 mL), and the resultant mixture was stirred at room temperature for 0.5 hour. At the same time 2,2,7-trimethyl-3,5-octanedione (H(tod), 2.792 g) was mixed with NaH (60% in mineral oil, 0.606 g) in ether (30 mL), and the mixture was also stirred at room temperature for 0.5 hours. The latter mixture (sodium 1,3-diketonate solution) was added to the former mixture, and the reaction mixture was stirred at room temperature overnight. The solvent (ether) was stripped off under reduced pressure. The resultant residue was treated with hexane (40 mL), and filtered. The filtrate was concentrated under reduced pressure (vacuum) to afford 6.02 g (crude yield: 95%) of crude product as a white solid. This solid was recrystallized in hexane (6 g of hexane) in the refrigerator (−38° C.) to give 3 g of first crop of pure product. The mother liquor can be used for further recrystallization to obtain additional product.

Example 2

Preparation of 1,3,4,5-Tetramethlylpyrazole(2,2,7-trimethyloctane-3,5-dionato)copper Cuprous chloride (0.605 g) was mixed with 1,3,4,5-tetramethlylpyrazole (0.76 g) in ether (20 mL), and the resultant mixture was stirred at room temperature for 0.5 h. At the same time 2,2,7-trimethyloctane-3,5-dione (H(tod), 1.127 g) was mixed with NaH (0.146 g) in ether (20 mL), and the mixture was also stirred at room temperature for 0.5 h. The latter mixture (sodium 1,3-diketonate solution) was added to the former mixture, and the reaction mixture was stirred at room temperature overnight. The initial yellow color gradually changed to green, then a brown color. The solvent (ether) was stripped off under reduced pressure, and the resultant residue was treated with hexane (30 mL), and dark brown solid was filtered. The green colored filtrate was concentrated under reduced pressure (vacuum) to afford 2.1 g (92%) of product as a green-colored solid. The solid was recrystallized in hexane (−38° C.) to provide a yellow solid (0.6 g) 1H NMR (300 MHz, $CD_2Cl_2$): d 5.37 (s, 1H), 3.84 (s, 3H), 2.31 (s, 3H), 2.17 (s, 3H), 2.05-2.00 (m, 3H), 1.93 (s, 1H), 1.25 (s, 9H), 0.91 (d, J=7.5 Hz, 6H), $^{13}$C NMR (75 MHz, $CD_2Cl_2$): d 199.4, 192.8, 147.7, 138.5, 112.5, 94.3, 52.2, 41.2, 36.6, 28.7, 27.3, 23.0, 12.8, 10.2, 8.3.

Example 3

Preparation of Bis(trimethylsilyl)acetylene (3-hexyl-2,4-pentanedionato)copper

Cuprous chloride (0.445 g) was mixed with bistrimethylsilylacetylene (0.92 g) in ether (20 mL), and the resultant mixture was stirred at room temperature for 0.5 h. At the same time 3-hexyl-2,4-pentanedione (0.858 g) was mixed with NaH (0.112 g) in ether (20 mL), and the mixture was also stirred at room temperature for 0.5 h. The latter mixture (sodium 1,3-diketonate solution) was added to the former mixture, and the reaction mixture was stirred at room temperature overnight. The solvent (ether) was stripped off under reduced pressure, and the resultant residue was treated with hexane (30 mL), and the dark brown solid was filtered. The filtrate was concentrated under reduced pressure (vacuum) to afford 1.72 g (92%) of product as a colorless liquid.

Example 4

Deposition of Copper Film

A reaction tube was charged with bis(trimethylsilyl)acetylene (3-hexyl-2,4-pentanedionato)copper (0.1 g), anhydrous dodecane (5 mL), and $CO_2$ (1000 psi). The solution was heated at 120° C. for 2 h to afford a reflective copper film on the walls of the reaction tube.

What is claimed is:

1. A method for depositing a copper-containing film on a surface of a substrate, comprising the steps of:
    i) dissolving a copper-containing precursor in a solvent, wherein the dissolving results in a supercritical or near-supercritical solution;
    wherein the precursor has a structural unit represented by Structure 1; and

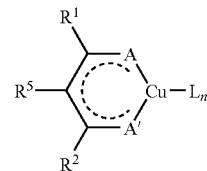

Structure 1 wherein L is a neutral ligand selected from a group consisting of alkynes, alkenes, nitriles, diazabutadiene and aromatic nitrogen heterocycles selected from a group consisting of pyridines, pyrazines, triazines, and N-substituted imidazoles, pyrazoles and triazoles;
    n=0.5, 1, or 2;
    $R^1$ and $R^2$ are independently selected from a group consisting of t-butyl, iso-butyl and neopentyl;
    A is O (oxygen) or $NR^3$;
    A' is O (oxygen) or $NR^4$;
    $R^3$ and $R^4$ are independently selected from a group consisting of methyl, ethyl, and n-propyl; and
    $R^5$ is H or C6-C9 alkyl;
    ii) contacting the substrate with the solution;
    iii) heating the substrate to a temperature between about 60° C. and less than 150° C.; and
    iv) forming a copper-containing film on at least a portion of the substrate surface.

2. The method of claim 1, wherein the substrate is a porous solid.

3. The method of claim 1, wherein the substrate comprises copper, silicon or silicon dioxide 4. The method of claim 3, wherein the substrate further comprises a barrier layer.

5. The method of claim 1, wherein the solvent comprises carbon dioxide.

6. The method of claim 5, wherein the solvent further comprises a co-solvent.

7. The method of any of claims 1-6, wherein the forming comprises a disproportionation reaction.

* * * * *

UNITED STATES PATENT AND TRADEMARK OFFICE
CERTIFICATE OF CORRECTION

| | | |
|---|---|---|
| PATENT NO. | : 7,550,179 B2 | Page 1 of 1 |
| APPLICATION NO. | : 11/215256 | |
| DATED | : June 23, 2009 | |
| INVENTOR(S) | : Jeffery Scott Thompson, Alexander Zak Bradley and Kyung-Ho Park | |

It is certified that error appears in the above-identified patent and that said Letters Patent is hereby corrected as shown below:

Title page, Item [75]
Please correct inventor's name from Jeffrey Scott Thompson to Jeffery Scott Thompson.

Signed and Sealed this

Twenty-eighth Day of July, 2009

JOHN DOLL
*Acting Director of the United States Patent and Trademark Office*